United States Patent [19]

Gericke et al.

[11] Patent Number: 5,731,351
[45] Date of Patent: Mar. 24, 1998

[54] ALKENYL-BENZOYLGUANIDINE DERIVATIVES

[75] Inventors: Rolf Gericke, Seeheim; Manfred Baumgarth, Darmstadt; Klaus-Otto Minck, Ober-Ramstadt; Norbert Beier, Reinheim, all of Germany

[73] Assignee: Merck Patent Gesellschaft mit Beschrankter Haftung, Darmstadt, Germany

[21] Appl. No.: 701,993

[22] Filed: Aug. 23, 1996

[30] Foreign Application Priority Data

Aug. 24, 1995 [DE] Germany .................. 195 31 138.8

[51] Int. Cl.$^6$ .................. C07C 279/22; C07C 277/08; A61K 31/155
[52] U.S. Cl. .................. 514/618; 514/619; 514/621; 514/821; 514/824; 514/866; 514/893; 558/412; 558/413; 558/415; 564/134; 564/139; 564/142; 564/162; 564/163; 564/166; 564/167
[58] Field of Search .................. 564/162, 134, 564/139, 142, 163, 166, 167; 514/618, 821, 824, 866, 893, 619, 621; 558/412, 413, 415

[56] References Cited

U.S. PATENT DOCUMENTS 5,571,842  11/1996  Kleemann et al. .................. 514/618

FOREIGN PATENT DOCUMENTS 416 499   9/1990  European Pat. Off. .
0 577 024  1/1994  European Pat. Off. .

OTHER PUBLICATIONS

Kuno et al., "Benzoylguanidine Derivatives as Medicaments Inhibiting Cellular Na +/H+ exchange", Chem. Abst. vol. 125, No. 3, 1996.

*Primary Examiner*—Peter O'Sullivan
*Attorney, Agent, or Firm*—Millen, White, Zelano & Branigan, P.C.

[57] ABSTRACT

Alkyl-benzoylguanidines of the formula I

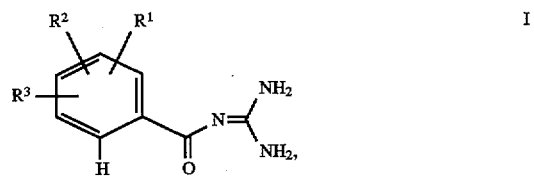

wherein $R^1$, $R^2$ and $R^3$ have the meanings given, and physiologically acceptable salts thereof show antiarrhythmic properties and act as inhibitors of the cellular $Na^+/H^+$ antiporter.

18 Claims, No Drawings

ALKENYL-BENZOYLGUANIDINE DERIVATIVES

The invention relates to alkenyl-benzoylguanidine derivatives of the formula 1

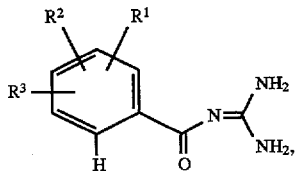

wherein $R^1$ and $R^2$ in each case independently of one another are H, Hal, A, CN, $NO_2$, $CF_3$, $CH_2F$, $CHF_2$, $C_2F_5$, $CH_2CF_3$ or $SO_n$—$R_4$, $R^3$ is —$CR^5$=$CR^6R^7$, —$C(R^6R^5)$—$CR^7$=$CR^9R^8$, —$C(R^6R^5)$—$C(R^7R^8)$—$CR^9$=$CR^{10}R^{11}$ or cycloalkenyl having 3–7 C atoms or cycloalkenylalkyl having 4–8 C atoms, $R^4$ is A or Ph, $R^5$, $R^6$, $R^7$, $R^8$, $R^9$, $R^{10}$, and $R^{11}$ in each case independently of one another are H or A, A is alkyl having 1 to 6 C atoms Hal is F, Cl, Br or I, Ph is phenyl which is unsubstituted or mono-, di- or trisubstituted by A, OA, $NH_2$, $NR^4R^5$, F, Cl, Br, I or $CF_3$ and n is 1 or 2, and physiologically acceptable salts thereof.

The invention was based on the object of discovering new compounds having valuable properties, in particular those which can be used for the preparation of medicaments.

It has been found that the compounds of the formula I and their physiologically acceptable salts have valuable pharmacological properties, coupled with a good tolerability.

The new compounds are inhibitors of the cellular Na+/H+ antiporter, that is to say active compounds which inhibit the Na+/H+ exchange mechanism of cells (Düsing et al., Med. Klin. 87, 378–384 (1992)) and which are thus good antiarrhythmics which are particularly suitable for the treatment of arrhythmias which occur as a consequence of oxygen deficiency.

The best-known active compound of the acylguanidine group is amiloride. However, this substance primarily shows an antihypertensive and saluretic action, which is particularly undesirable in the treatment of disturbances in cardiac rhythm, while the antiarrhythmic properties are only very weak. Structurally similar compounds are furthermore known, for example from EP 04 16 499.

The invention relates to compounds of the formula I and their physiologically acceptable salts.

The novel substances of the invention show a good cardioprotective action and are therefore the diseases caused primarily or secondarily by this damage can be treated. The active compounds are also particularly suitable for preventive uses.

On the basis of the protective actions of these substances in pathological hypoxic or ischaemic situations, further possible uses result from these in surgical operations for protection of temporarily under-supplied organs, in organ transplants for protection of the organs removed, in angioplastic operations on vessels or the heart, in ischaemias of the nervous system, in the treatment of states of shock and for preventive avoidance of essential hypertension.

The compounds can furthermore also be employed as therapeutics for diseases caused by cell proliferation, such as arterial sclerosis, delayed diabetic complications, tumor diseases, fibrotic diseases, in particular of the lung, liver and kidneys, and organ hypertrophies and hyperplasias. The substances moreover are suitable for diagnostic use for detection of diseases which are accompanied by an increased activity of the Na+/H+ antiporter, for example in erythrocytes, platelets or leucocytes.

The actions of the compounds can be determined with the aid of methods known per se, such as are described, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Suitable test animals are, for example, mice, rats, guinea-pigs, dogs, cats, monkeys or pigs.

The compounds may, therefore, be used as pharmaceutically active compounds in human and veterinary medicine. In addition, they can be used as intermediates for preparing further pharmaceutically active compounds.

In the formulae given, A is a branched or unbranched alkyl group having 1–6, preferably 1–4, in particular 1,2 or 3, C atoms, specifically preferably methyl, and furthermore preferably ethyl, propyl, isopropyl, butyl or isobutyl, and moreover preferably sec-butyl, tert-butyl, pentyl, isopentyl (3-methylbutyl), hexyl or isohexyl (4-methylpentyl).

$R^1$ is preferably H, A or Hal, in particular Br or Cl. $R^1$ is particularly preferably methyl or ethyl. Furthermore, however, also preferably $CH_2F$, $CHF_2$, $CF_3$ or $C_2F_5$. $R^1$ is preferably located in the ortho-position relative to the guanidine group.

$R^2$ is preferably —$SO_2$—A, $CF_3$, Cl, Br or $NO_2$. $R^2$ is particularly preferably —$SO_2$—$CH_3$.

The radical $R^2$ is preferably in the 3- or 5-position relative to the benzoylguanidine group.

$R^3$ is preferably —$CR^5$=$CR^6R^7$ or —$C(R^6R^5)$—$CR^7$=$CR^9R^8$.

$R^3$ is furthermore also preferably cyclopropenyl, cyclobutenyl, 3-cyclopentenyl, 4-cyclopentenyl, 3- or 4-cyclohexenyl, 3-, 4- or 5-cycloheptenyl or a corresponding cycloalkenylmethyl derivative.

$R^4$ is preferably methyl, ethyl or phenyl.

Ph is preferably phenyl which is unsubstituted or monosubstituted by Cl, Br, A, OA, $NH_2$, NHA, $NA_2$ or $CF_3$.

$R^5$ to $R^{11}$ preferably in each case independently of one another are H and/or A, in particular hydrogen and/or methyl.

Hal is preferably F, Cl or Br.

Generally, all the radicals such as, for example, $R^5$ to $R^{11}$ which occur severally can be identical or different, that is to say are independent of one another.

The compounds can be in the form of cis/trans isomers. The present invention includes both mixtures and the pure cis and trans forms of the compounds. The compounds can furthermore also be in the form of racemates, which can be separated into enantiomers.

The invention accordingly relates particularly to those compounds of the formula I in which at least one of the radicals mentioned has one of the abovementioned preferred meanings. Some preferred groups of compounds can be expressed by the following formulae Ia to Ih, which correspond to the formula I and wherein the radicals not described in more detail have the meaning given in the case of the formula I, but wherein in Ia $R^1$ is A and $R^2$ is —$SO_2$—A, $NO_2$ or $CF_3$;

in Ib $R^1$ is H or Hal and $R_2$ is —$SO_2A$, $NO_2$ or $CF_3$;

in Ic $R^1$ is A or H, $R^2$ is —$SO_2A$ and $R^3$ is —$CR^5$=$CR^6R^7$, where $R^5$ to $R^7$ in each case independently of one another are H or methyl;

in Id $R^1$ is A or H, $R^2$ is —$SO_2$—A and $R^3$ is —$C(R^5R^6)$ —$CR^7$=$CR^8 R^9$ where $R^5$ to $R^9$ in each case independently of one another are H or methyl;

in Ie $R^1$ is A or H, $R^2$ is —$SO_2$—A and $R^3$ is —$C(R^5 R^6)$—$C(R^7R^8)$—$CR^9$=$CR^{10}R^{11}$, where $R^5$ to $R^{11}$ in each case independently of one another are H or methyl;

in If $R^1$ is H or A and is in the ortho-position relative to the benzoylguanidine group and $R^2$ is —$SO_2$—A and is in the meta-position relative to the benzoylguanidine group;

in Ig $R^3$ is cycloalkenyl having 3–7 C atoms and is in the para-position relative to the benzoylguanidine group and $R^2$ is in the meta-position relative to the benzoylguanidine group and is —$SO_2$—A;

in Ih $R^1$ is A or H, $R^2$ is —$SO_2$—A, $R^3$ is cycloalkenyl having 3 to 7 C atoms and $R^3$ is located in the para-position relative to the benzoylguanidine group.

The invention furthermore relates to a process for the preparation of the compounds of the formula I according to claim 1 and of salts thereof, characterized in that a compound of the formula II

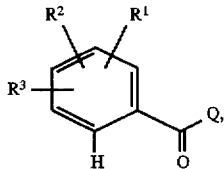

wherein $R^1$, $R^2$ and $R^3$ have the abovementioned meanings and

Q is Cl, Br, OA, O—CO—A, O—CO—Ph, OH or another reactive esterified OH group or leaving group which can easily be replaced nucleophilically, is reacted with guanidine, or in that a benzoylguanidine of the formula III

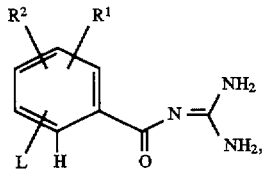

wherein $R^1$ and $R^2$ have the abovementioned meanings and

L is F, Cl, Br or I, is reacted with an unsaturated hydrocarbon compound of the formula IV $R^3$—H        IV wherein $R^3$ has the meaning given, in the presence of a transition metal catalyst and if appropriate of an activator, or in that a compound which otherwise corresponds to the formula I but which contains, instead of one or more hydrogen atoms, one or more reducible group(s), such as, for example, an alkynyl group, and/or one or more additional C—C and/or C—N bond(s) is treated with a reducing agent, or in that a compound which otherwise corresponds to the formula I but which contains, instead of one or more hydrogen atoms, one or more solvolyzable group(s) is treated with a solvolyzing agent, or in that a radical $R^3$ is converted into another radical $R^3$ by isomerization, by rearranging a double bond under the action of a transition metal catalyst and/or of a metal carbonyl, and/or in that a base of the formula I obtained is converted into one of its salts by treatment with an acid.

The compounds of the formula I are otherwise prepared by methods known per se, such as are described in the literature, (for example in the standard works such as Houben-Weyl, Methoden der organischen Chemie [Methods of organic chemistry], Georg-Thieme-Verlag, Stuttgart; Organic Reactions, John Wiley & Sons, Inc., New York; and in the abovementioned patent application), and in particular under reaction conditions which are known and suitable for the reactions mentioned. It is also possible to utilize variants of these methods which are known per se and are not mentioned in more detail here.

If desired, the starting substances can also be formed in situ such that they are not isolated from the reaction mixture but are immediately reacted further to give the compounds of the formula I.

Compounds of the formula I are preferably prepared by reacting an activated carboxylic acid derivative of the formula II, wherein Q is particularly preferably Cl or —O—$CH_3$, with ghanidine. Reaction variants in which the free carboxylic acid II (Q=OH) is reacted in a manner known per se to give the particular activated derivative and this is then reacted directly with guanidine, without intermediate isolation, are also particularly suitable. Methods in which an intermediate isolation is not necessary are, for example, activation with carbonyldiimidazole or dicyclohexylcarbodiimide or the Mukayama variant (Angew. Chem. 91, 788–812 (1979)).

The carboxylic acids and carboxylic acid derivatives of the formula II are as a rule known. They are prepared, in particular, by the Heck reaction, J. Org. Chem. 46, 1067 (1981) or by Pd-catalyzed cross-coupling. Preferred catalysts are, for example, Pd $(PPh_3)_4$, $(Ph_3P)_2PdCl_2$, $Pd(CH_3COO)_2$ or Pd-(II)-[1,1'-bis-(diphenylphosphine) ferrocene] chloride, preferably in the presence of CuI.

The carboxylic acids of the formula II and derivatives thereof are furthermore prepared by metallizing suitable benzoic acid derivatives of the formula V

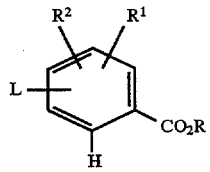

wherein $R^1$, $R^2$ and L have the meanings given and R is H or A, and then reacting the product with a corresponding alkenyl halide. A suitable base for the metallization is, for example, lithium diisopropylamide.

In the abovementioned cross-couplings, a carboxylic acid derivative or an ester derivative of the formula V wherein L is preferably Cl, Br or I is reacted with an organometallic alkenyl compound, which is prepared in situ by metallization, in the presence of a suitable metal catalyst, in particular one of those mentioned above.

The reaction is carried out analogously to the reaction of the compounds III and IV. It is described below.

However, a compound of the formula II is particularly preferably prepared by the Heck reaction, which is described, for example, in J. Org. Chem. 46, 1067 (1981) for example by reacting a compound of the formula V wherein L is Br or I with the cyclic or linear alkenyl compound in the presence of a Pd(II) salt, for example the acetate, and a phosphine, for example tri-o-tolylphosphine.

The reaction of a reactive carboxylic acid derivative of the formula II with guanidine is carried out in a manner known per se, preferably in a protic or aprotic polar or non-polar inert organic solvent.

Suitable solvents are mentioned below for the reaction of the compounds III and IV. Particularly preferred solvents are, however, methanol, tetrahydrofuran, dimethoxyethane, dioxane or mixtures which can be prepared from these, as well as water. Temperatures between 20° C. and the boiling point of the solvent, for example, are suitable as the reaction temperature. The reaction times are between 5 minutes and 12 hours. It is expedient to employ an acid-trapping agent in the reaction. Any types of bases which do not interfere with the reaction itself are suitable for this. However, the use of inorganic bases, such as potassium carbonate, or of organic bases, such as triethylamine or pyridine, or an excess of the guanidine is particularly suitable.

Compounds of the formula I according to claim 1 can furthermore be prepared by reacting a benzoylguanidine of the formula III with a compound of the formula IV. The starting substances of the formula III can be prepared in a simple manner by reaction of correspondingly substituted benzoic acids or reactive acid derivatives which can be derived therefrom, such as, for example, acid halides, esters or anhydrides, with guanidine under reaction conditions such as are known per se and generally customary for amide preparation. Those reaction variants such as are mentioned above for the reaction of compound II with guanidine are in turn particularly suitable.

The compounds of the formula IV are known per se, as are the methods for their preparation. If they are not known, they can be prepared by methods known per se.

The preparation of the compound II and the reaction of the compound III with a compound of the formula IV are carried out in a manner known per se, preferably in a protic or aprotic polar inert organic solvent.

It is likewise expedient to carry out the preparation of II or the reaction of III with IV in the presence of a base or with an excess of the basic component. Preferred suitable bases are, for example, alkali metal or alkaline earth metal hydroxides, carbonates, or alcoholates or organic bases, such as triethylamine or pyridine, which can also be used in excess and can then simultaneously serve as the solvent.

Suitable inert solvents are, in particular, alcohols, such as methanol, ethanol, isopropanol, n-butanol or tert-butanol; ethers, such as diethyl ether, diisopropyl ether, tetrahydrofuran (THF) or dioxane; glycol ethers, such as ethylene glycol monomethyl or monoethyl ether (methylglycol or ethylglycol) or ethylene glycol dimethyl ether (diglyme); ketones, such as acetone or butanone; nitriles, such as acetonitrile; nitro compounds, such as nitromethane or nitrobenzene; esters, such as ethyl acetate; amides, such as phosphoric acid hexamethyltriamide, sulfoxides, such as dimethyl sulfoxide (DMSO); chlorinated hydrocarbons, such as methylene chloride, chloroform, trichloroethylene, 1,2-dichloroethane or carbon tetrachloride; and hydrocarbons, such as benzene, toluene or xylene. Mixtures of these solvents with one another are also suitable.

The Heck reaction usually requires increased temperatures (100°–150° C.).

A particularly preferred procedure in the reaction of III with IV comprises dissolving the corresponding benzoylguanidine and the unsaturated hydrocarbon compound in dimethylformamide together with a Pd(II) catalyst and a triphenylphosphine derivative and then heating the solution. If the alkene is gaseous, the gas is passed in throughout the entire reaction time. In this case, the reaction can preferably also be carried out in an autoclave.

The compounds of the formula I can furthermore be obtained by liberating them from their functional derivatives by solvolysis, in particular hydrolysis, or by hydrogenolysis.

Preferred starting substances for the solvolysis or hydrogenolysis are those which otherwise correspond to the formula I but which comprise, instead of one or more free amino and/or hydroxyl groups, corresponding protected amino and/or hydroxyl groups, preferably those which carry, instead of an H atom which is bonded to an N atom, an amino-protective group, in particular those which carry, instead of an HN group, an R'-N group, wherein R' is an amino-protective group, and/or those which carry, instead of the H atom of a hydroxyl group, a hydroxy-protective group, for example those which correspond to the formula I but carry, instead of an OH group, an OR" group, wherein R" is a hydroxy-protective group.

It is also possible for several—identical or different— protected amino and/or hydroxyl groups to be present in the molecule of the starting substance. If the protective groups present differ from one another, they can in many cases be split off selectively.

The term "amino-protective group" is generally known and relates to groups which are suitable for protecting (blocking) an amino group from chemical reactions, but which can easily be removed after the desired chemical reaction elsewhere in the molecule has been carried out. Typical such groups are, in particular, unsubstituted or substituted acyl, aryl (for example 2,4-dinitrophenyl (DNP), aralkoxymethyl (for example benzyloxymethyl (BOM) or aralkyl groups (for example benzyl, 4-nitrobenzyl or triphenylmethyl). Since the amino-protective groups are removed after the desired reaction (or reaction sequence), their nature and size is otherwise not critical; however, those having 1–20, in particular 1–8, C atoms are preferred. The term "acyl group" is to be interpreted in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and above all, aralkoxycarbonyl groups. Examples of such acyl groups are alkanoyl, such as acetyl, propionyl or butyryl; aralkanoyl, such as phenylacetyl; aroyl, such as benzoyl or toluoyl; aryloxyalkanoyl, such as phenoxyacetyl; alkoxycarbonyl, such as methoxycarbonyl, ethoxycarbonyl, 2,2,2-trichloroethoxycarbonyl, isopropoxycarbonyl, tert-butoxycarbonyl (BOC), or 2-iodoethoxycarbonyl; or aralkyloxycarbonyl, such as benzyloxycarbonyl (CBZ), 4-methoxybenzyloxycarbonyl, or 9-fluorenylmethoxycarbonyl (FMOC). Preferred amino-protective groups are BOC, DNP and BOM, and furthermore CBZ, benzyl and acetyl.

The term "hydroxy-protective group" is also generally known and relates to groups which are suitable for protecting a hydroxyl group against chemical reactions but which can easily be removed after the desired chemical reaction has been carried out elsewhere in the molecule. Typical such groups are the abovementioned unsubstituted or substituted aryl, aralkyl or acyl groups, and furthermore also alkyl groups. The nature and size of the hydroxy-protective groups is not critical, since they are removed again after the desired chemical reaction or reaction sequence; groups having 1–20, in particular 1–10, C atoms are preferred. Examples of hydroxy-protective groups are, inter alia, tert-butyl, benzyl, p-nitrobenzoyl, p-toluenesulfonyl and acetyl, benzyl and acetyl being particularly preferred.

The functional derivatives of the compounds of the formula I to be used as starting substances can be prepared by customary methods, such as are described, for example, in the standard works and patent applications mentioned, for example by reaction of compounds which correspond to the formulae II and III but in which at least one of these compounds contains a protective group instead of an H atom.

The liberation of the compounds of the formula I from their functional derivatives is achieved—depending on the protective group used—with, for example, strong acids, expediently with trifluoroacetic acid or perchloric acid, but also with other strong inorganic acids, such as hydrochloric acid or sulfuric acid, strong organic carboxylic acids, such as trichloroacetic acids, or sulfonic acids, such as benzene- or p-toluenesulfonic acid. The presence of an additional inert solvent is possible but not always necessary.

Suitable inert solvents are preferably organic, for example carboxylic acids, such as acetic acid, ethers, such as tetrahydrofuran (THF) or dioxane, amides, such as dimethylformamide (DMF), halogenated hydrocarbons, such as methylene chloride, and furthermore also alcohols, such as methanol, ethanol or isopropanol, as well as water. Mixtures of the abovementioned solvents are furthermore possible. Trifluoroacetic acid is preferably used in excess without addition of a further solvent, and perchloric acid is used in the form of a mixture of acetic acid and 70% perchloric acid in a ratio of 9:1. The reaction temperatures for the splitting reaction are expediently from about 0° C. to about 50° C.; the reaction is preferably carried out at from 15° C. to 30° C. (room temperature).

The BOC group can preferably be split off, for example, with 40% trifluoroacetic acid in methylene chloride or with about 3 to 5 N HCl in dioxane at 15°–60° C., and the FMOC group can be split off with an approximately 5–20% solution of dimethylamine, diethylamine or piperidine in DMF at 15°–50° C. The DNP group is also split off, for example, with an approximately 3–10% solution of 2-mercaptoethanol in DMF/water at 15°–30° C.

Protective groups which can be removed by hydrogenolysis (for example BOM, CBZ or benzyl) can be split off, for example, by treatment with hydrogen in the presence of a catalyst (for example a noble metal catalyst, such as palladium, expediently on a support, such as charcoal). Suitable solvents here are those mentioned above, in particular, for example, alcohols, such as methanol or ethanol, or amides, such as DMF. The hydrogenolysis is preferably carried out at temperatures from about 0° C. to 100° C. under pressures from about 1 to 200 bar, preferably at 20°–30° C. under 1–10 bar. Good hydrogenolysis of the CBZ group is achieved, for example, on 5–10% Pd-C in methanol at 20°–30° C.

The compounds of the formula I can furthermore be prepared by converting a corresponding precursor of a compound of the formula I into such a compound by reduction. Thus, for example, it is possible to convert a compound which corresponds per se to a compound of the formula I but has an alkynyl substituent instead of $R^3$ into a compound of the formula I by partial catalytic hydrogenation. Such reductions are preferably hydrogenated with hydrogen gas in the presence of a catalyst, such as, for example, Pd, Pt, a Lindlar catalyst and the like.

A compound of the formula I can furthermore be converted into another compound of the formula I by isomerizing a double bond in a substituent $R^3$. The isomerization is expediently carried out in the presence of a catalyst under the influence of heat. Suitable catalysts are, for example, salts of Pt or Pd, other transition metal catalysts, or metal carbonyls. Bis(benzonitrile)palladium(II) chloride, for example, is particularly preferred. The method is described by Durvasula et al. in Tetrahedron Lett. 22, 2337 (1981).

A base of the formula I can furthermore be converted into the associated acid addition salt with an acid. Acids which give physiologically acceptable salts are possible for this reaction. Thus, inorganic acids can be used, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids or laurylsulfuric acid.

The compounds of the formula I and their physiologically acceptable salts can be used for the preparation of pharmaceutical formulations, in particular by a nonchemical route. They can be brought into a suitable dosage form here together with at least one solid, liquid and/or semi-liquid carrier or auxiliary, and if appropriate in combination with one or more further active compound(s).

The invention furthermore relates to compositions, in particular pharmaceutical formulations, comprising at least one compound of the formula I and/or one of its physiologically acceptable salts.

The compounds may be used as pharmaceutical agents in a manner analogous to amiloride and other known acylguanidine compounds, but exhibiting the advantages described herein, e.g., inhibition of the cellular $Na^+/H^+$ exchange mechanism and activity in the treatment and prevention of disturbances of the cardiac rhythm. As intermediates, the compounds may be used to prepare pharmaceutically active compounds using synthetic methods analogous to those known in the art.

These formulations can be used as medicaments in human or veterinary medicine. Possible carriers are organic or inorganic substances which are suitable for enteral (for example oral), parenteral or topical administration and which do not react with the new compounds, for example water, vegetable oils, benzyl alcohols, polyethylene glycols, glycerol triacetate, gelatin, carbohydrates, such as lactose or starch, magnesium stearate, talc, lanolin and petroleum jelly. Tablets, coated tablets, capsules, syrups, juices or drops, in particular, are used for oral use, suppositories are used for rectal use, solutions, preferably oily or aqueous solutions, and furthermore suspensions, emulsions or implants, are used for parenteral use, and ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders are used for topical use. The new compounds can also be lyophilized and the resulting lyophilizates used, for example, for preparing injection preparations.

Liposomal formulations are also possible, in particular, for topical use. The formulations mentioned can be sterilized and/or comprise auxiliaries, such as lubricants, preservatives, stabilizers and/or wetting agents, emulsifiers, salts for influencing the osmotic pressure, buffer substances, colorants, flavoring and/or aroma substances. If desired, they can also comprise one or more other active compounds, for example one or more vitamins.

The compounds of the formula I and their physiologically acceptable salts can be administered to humans or animals, in particular mammals, such as monkeys, dogs, cats, rats or mice, and can be used for therapeutic treatment of the human or animal body and for combating diseases, in particular in the treatment and/or prophylaxis of disturbances of the cardiovascular system. They are therefore suitable for treatment of arrhythmias, in particular if these are caused by oxygen deficiency, of angina pectoris, infarctions and ischaemias of the nervous system, such as, for example, apoplexy or cerebral oedemas, or of states of shock and for preventive treatment.

The substances can furthermore be employed as therapeutics for diseases in which cell proliferations play a role, such as arteriosclerosis, delayed diabetic complications, tumor diseases, fibroses and organ hypertrophies and hyperplasias, in particular for diseases of the prostate.

The substances according to the invention are preferably administered here analogously to known antiarrhythmics, for example aprindine, preferably in dosages of between from 0.01 to 5 mg, in particular from 0.02 to 0.5 mg per dosage unit. The daily dosage is preferably from about 0.0001 to 0.1, in particular from 0.0003 to 0.01, mg/kg of body weight. However, the specific dose for each particular patient depends on the most diverse factors, for example on the efficacy of the specific compound employed, on the age, body weight, general state of health and sex, on the diet, on the administration time and route and on the rate of execretion, the drug combination and the severity of the particular disease to which the treatment applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 31 138.8, filed Aug. 24, 1995, are hereby incorporated by reference.

EXAMPLES

In the following examples, "customary working-up" means:

Water is added, if necessary, the mixture is extracted with an organic solvent, such as ethyl acetate, the organic phase is separated off, dried over sodium sulfate, filtered and evaporated and the residue is purified by chromatography and/or crystallization.

Example 1

A fresh guanidine solution prepared from 5.6 g of guanidinium chloride and 1.6 g of sodium in 40 ml of ethylene glycol dimethyl ether is added to a solution of 1.2 g of 2-methyl-4-(1-cyclopentene-3-yl)-5-methylsulfonylbenzoyl chloride [obtainable by reaction of methyl 2-methyl-4-bromo-5-methyl-sulfonyl-benzoate with cyclopentene in the presence of Pd(II)acetate and tri-o-tolylphosphine, separation of the two isomers by means of a Prebar® stainless steel cartridge 250-50, filled with LiChroprep RP-18; eluent 0.1 m $NaH_2PO_4$ buffer/acetonitrile 9:1 with an increasing gradient to 1:1, and subsequent hydrolysis and conversion into the acid chloride with $SOCl_2$], in 20 ml of ethylene glycol dimethyl ether with ice-cooling and the mixture is stirred at room temperature for 2 hours. The reaction mixture is then poured onto ice-water, acidified and washed with ethyl acetate and the pH of the solution is adjusted to 10. Customary working-up gives N-diaminomethylene-2-methyl-4-(1-cyclopentene-3-yl)-5-methylsulfonylbenzamide, which can be recrystallized from acetonitrile/diethyl ether, melting point 212°–214°.

Analogous reaction of guanidine gives with 2-methyl-4-(1-propene-1-yl)-5-methylsulfonylbenzoyl chloride,
N-diaminomethylene-2-methyl-4-(1-propene-1-yl)-5-methylsulfonylbenzamide, m.p. 202°–204°;

with 2-methyl-4-ethenyl-5-methylsulfonylbenzoyl chloride,
N-diaminomethylene-2-methyl-4-ethenyl-5-methylsulfonylbenzamide;

with 2-methyl-4-(1-propene-2-yl)-5-methylsulfonylbenzoyl chloride,
N-diaminomethylene-2-methyl-4-(propene-2-yl)-5-methylsulfonylbenzamide, m.p. 168°;

with 2-methyl-4-(1-propen-3-yl)-5-methylsulfonylbenzoyl chloride,
N-diaminomethylene-2-methyl-4-(propen-3-yl)-5-methylsulfonylbenzamide;

with 2-methyl-4-(1-buten-4-yl)-5-methylsulfonylbenzoyl chloride,
N-diaminomethylene-2-methyl-4-(1-buten-4-yl)-5-methylsulfonylbenzamide;

with 2-methyl-4-(2-methyl-1-propen-1-yl)-5-methylsulfonylbenzoyl chloride,
N-diaminomethylene-2-methyl-4-(1-propen-1-yl)-5-methylsulfonylbenzamide;

with 2-methyl-4-(2-buten-1-yl)-5-methylsulfonylbenzoyl chloride,
N-diaminomethylene-2-methyl-4-(2-buten-1-yl)-5-methylsulfonylbenzamide;

with 2-methyl-4-(2-buten-2-yl)-5-methylsulfonylbenzoyl chloride,
N-diaminomethylene-2-methyl-4-(2-buten-2-yl)-5-methylsulfonylbenzamide;

with 2-methyl-4-(3-methyl-2-buten-2-yl)-5-methylsulfonylbenzoyl chloride,
N-diaminomethylene-2-methyl-4-(3-methyl-2-buten-2-yl)-5-methylsulfonylbenzamide;

with 2-methyl-4-(3-buten-3-yl)-5-methylsulfonylbenzoyl chloride,
N-diaminomethylene-2-methyl-4-(1-buten-3-yl)-5-methylsulfonylbenzamide, m.p. 186°–188°;

with 2-methyl-4-(1-buten-1-yl)-5-methylsulfonylbenzoyl chloride,
N-diaminomethylene-2-methyl-4-(1-buten-1-yl)-5-methylsulfonylbenzamide;

with 2-methyl-4-(1-buten-2-yl)-5-methylsulfonylbenzoyl chloride,
N-diaminomethylene-2-methyl-4-(1-buten-2-yl)-5-methylsulfonylbenzamide;

with 2-methyl-4-(1-buten-3-yl)-5-methylsulfonylbenzoyl chloride,

N-diaminomethylene-2-methyl-4-(1-buten-3-yl)-5-methylsulfonylbenzamide;

with 2-methyl-4-(1-penten-1-yl)-5-methylsulfonylbenzoyl chloride,

N-diaminomethylene-2-methyl-4-(1-penten-1-yl)-5-methylsulfonylbenzamide;

with 2-methyl-4-(1-cyclopenten-4-yl)-5-methylsulfonylbenzoyl chloride,

N-diaminomethylene-2-methyl-4-(1-cyclopenten-4-yl)-5-methylsulfonylbenzamide, m.p. 198°;

with 2-methyl-4-(2-penten-1-yl)-5-methylsulfonylbenzoyl chloride,

N-diaminomethylene-2-methyl-4-(2-penten-1-yl)-5-methylsulfonylbenzamide;

with 2-methyl-4-(3-penten-1-yl)-5-methylsulfonylbenzoyl chloride,

N-diaminomethylene-2-methyl-4-(3-penten-1-yl)-5-methylsulfonylbenzamide;

with 2-methyl-4-(1-hexen-1-yl)-5-methylsulfonylbenzoyl chloride,

N-diaminomethylene-2-methyl-4-(1-hexen-1-yl)-5-methylsulfonylbenzamide;

with 2-methyl-4-(2-hexen-1-yl)-5-methylsulfonylbenzoyl chloride,

N-diaminomethylene-2-methyl-4-(2-hexen-1-yl)-5-methylsulfonylbenzamide;

with 2-methyl-4-(3-hexen-1-yl)-5-methylsulfonylbenzoyl chloride,

N-diaminomethylene-2-methyl-4-(3-hexen-1-yl)-5-methylsulfonylbenzamide;

Example 2

Analogously to Example 1, by reaction of 1.8 g of 2-ethyl-4-(1-cyclopenten-3-yl)-5-methylsulfonylbenzoylchloride with guanidine, customary working up gives N-diaminomethylene-2-ethyl-4-(1-cyclopenten-3-yl)-5-methylsulfonylbenzamide which can be recrystallized from acetonitrile/diethyl ether.

Analogous reaction of guanidine gives with 2-ethyl-4-(1-propen-1-yl)-5-methylsulfonyl-benzoyl chloride N-diaminomethylene-2-ethyl-4-(1-propen-1-yl)-5-methylsulfonylbenzamide;

with 2-ethyl-4-ethenyl-5-methylsulfonyl-benzoyl chloride

N-diaminomethylene-2-ethyl-4-ethenyl-5-methylsulfonylbenzamide;

with 2-ethyl-4-(1-propen-2-yl)-5-methylsulfonyl-benzoyl chloride

N-diaminomethylene-2-ethyl-4-(1-propen-2-yl)-5-methylsulfonylbenzamide;

with 2-ethyl-4-(1-propen-3-yl)-5-methylsulfonyl-benzoyl chloride

N-diaminomethylene-2-ethyl-4-(1-propen-3-yl)-5-methylsulfonylbenzamide;

with 2-ethyl-4-(1-buten-4-yl)-5-methylsulfonyl-benzoyl chloride

N-diaminomethylene-2-ethyl-4-(1-buten-4-yl)-5-methylsulfonylbenzamide;

with 2-ethyl-4-(2-ethyl-1-propen-1-yl)-5-methyl-sulfonylbenzoyl chloride

N-diaminomethylene-2-ethyl-4-(2-ethyl-1-propen-1-yl)-5-methylsulfonylbenzamide;

with 2-ethyl-4-(1-buten-1-yl)-5-methylsulfonyl-benzoyl chloride

N-diaminomethylene-2-ethyl-4-(2-buten-1-yl)-5-methylsulfonylbenzamide;

with 2-ethyl-4-(2-buten-2-yl)-5-methylsulfonyl-benzoyl chloride

N-diaminomethylene-2-ethyl-4-(2-buten-2-yl)-5-methylsulfonylbenzamide;

with 2-ethyl-4-(3-methyl-2-buten-2-yl)-5-methyl-sulfonylbenzoyl chloride

N-diaminomethylene-2-ethyl-4-(3-methyl-2-buten-2-yl)-5-methylsulfonylbenzamide;

with 2-ethyl-4-(1-buten-3-yl)-5-methylsulfonyl-benzoyl chloride

N-diaminomethylene-2-ethyl-4-(1-buten-3-yl)-5-methylsulfonylbenzamide;

with 2-ethyl-4-(1-buten-1-yl)-5-methylsulfonyl-benzoyl chloride

N-diaminomethylene-2-ethyl-4-(1-buten-1-yl)-5-methylsulfonylbenzamide;

with 2-ethyl-4-(1-buten-2-yl)-5-methylsulfonyl-benzoyl chloride

N-diaminomethylene-2-ethyl-4-(1-buten-2-yl)-5-methylsulfonylbenzamide;

with 2-ethyl-4-(1-buten-3-yl)-5-methylsulfonyl-benzoyl chloride

N-diaminomethylene-2-ethyl-4-(1-buten-3-yl)-5-methylsulfonylbenzamide;

with 2-ethyl-4-(1-penten-1-yl)-5-methylsulfonyl-benzoyl chloride

N-diaminomethylene-2-ethyl-4-(1-penten-1-yl)-5-methylsulfonylbenzamide;

with 2-ethyl-4-(2-penten-1-yl)-5-methylsulfonyl-benzoyl chloride

N-diaminomethylene-2-ethyl-4-(2-penten-1-yl)-5-methylsulfonylbenzamide;

with 2-ethyl-4-(3-penten-1-yl)-5-methylsulfonyl-benzoyl chloride

N-diaminomethylene-2-ethyl-4-(3-penten-1-yl)-5-methylsulfonylbenzamide;

with 2-ethyl-4-(1-hexen-1-yl)-5-methylsulfonyl-benzoyl chloride

N-diaminomethylene-2-ethyl-4-(1-hexen-1-yl)-5-methylsulfonylbenzamide;

with 2-ethyl-4-(2-hexen-1-yl)-5-methylsulfonyl-benzoyl chloride

N-diaminomethylene-2-ethyl-4-(2-hexen-1-yl)-5-methylsulfonylbenzamide;

with 2-ethyl-4-(3-hexen-1-yl)-5-methylsulfonyl-benzoyl chloride

N-diaminomethylene-2-ethyl-4-(3-hexen-1-yl)-5-methylsulfonylbenzamide;

Example 3

80 ml of cyclopentene are added to a suspension of 32 g of N-diaminomethylene-2-methyl-4-bromo-5-methylsulfonylbenzamide [obtainable by reaction of 2-methyl-4-bromo-5-methylsulfonylbenzoyl chloride with guanidine], 40 ml of triethylamine, 0.4 g of Pd(II) acetate, 0.8 g of tri-o-tolylphosphine and 80 ml of dimethylformamide (DMF), and the reaction mixture is heated at 100°–110° for 8 hours. The solvent is then removed, 300 ml of water are added, the mixture is acidified and washed several times with ethyl acetate and the pH of the solution is adjusted to 10.

Customary working up gives an isomer mixture of N-diaminomethylene-2-methyl-4-(1-cyclopenten-3-yl)-5-methylsulfonylbenzamide (88%) and N-diaminomethylene-2-methyl-4-(1-cyclopenten-4-yl)-5-methylsulfonylbenzamide (15%). For separation of the isomers, the mixture is introduced on to a Prebar® stainless steel cartridge 250-50, filled with LiChroprep RP-18, and eluted with 0.1 m $NaH_2PO_4$ buffer/acetonitrile in a ratio of 9:1 with an increasing gradient up to a ratio of 1:1.

Isomer 1: N-diaminomethylene-2-methyl-4-(1-cyclopenten-3-yl)-5-methylsulfonylbenzamide, m.p. 212°–214°

Isomer 2: N-diaminomethylene-2-methyl-4-(1-cyclopenten-4-yl)-5-methylsulfonylbenzamide.

Example 4

700 mg of N-diaminomethylene-2-methyl-4-(1-cyclopenten-3-yl)-5-methylsulfonylbenzamide [which can be prepared according to Example 1; m.p. 212°–214°] are dissolved in 20 ml of acetone, and 6.1 ml of methanesulfonic acid are added, while stirring. Filtration and lyophilization give N-diaminomethylene-2-methyl-4-(1-cyclopenten-3-yl)-5-methylsulfonylbenzamide, methane-sulfonate, m.p. 202°–204°.

The following methanesulfonates are obtained analogously from the free bases:

N-diaminomethylene-4-(1-cyclopenten-3-yl)-5-methylsulfonylbenzamide, methanesulfonate, m.p. 225°;

N-diaminomethylene-2-methyl-4-(1-cyclopenten-1-yl)-5-methylsulfonylbenzamide, methanesulfonate, m.p. 218°–220°;

N-diaminomethylene-2-methyl-4-(1-propene-1-yl)-5-methylsulfonylbenzamide, methanesulfonate, m.p. 207°–209°;

N-diaminomethylene-2-methyl-4-(1-cyclopentenyl-4-yl)-5-methylsulfonylbenzamide, methanesulfonate, m.p. 186°;

N-diaminomethylene-2-methyl-4-(1-buten-3-yl)-5-methylsulfonylbenzamide, methanesulfonate, m.p. 122°;

N-diaminomethylene-4-(1-propenyl-1-yl)-5-methylsulfonylbenzamide, methanesulfonate, m.p. 250°–252°;

N-diaminomethylene-2-methyl-4-(1-propenyl-2-yl)-5-methylsulfonylbenzamide, methanesulfonate, m.p. 172°.

Example 5

Analogously to Example 1, by reaction of 2.2 g of 3-methylsulfonyl-4-(1-cyclopenten-3-yl)-benzoyl chloride with guanidine, customary working up gives N-diaminomethylene-3-methylsulfonyl-4-(1-cyclopenten-3-yl)benzamide, which can be recrystallized from acetonitrile/diethylether, m.p. 188°–190°.

Analogous reaction of guanidine gives with 3-methylsulfonyl-4-(1-propen-1-yl)benzoyl chloride,
   N-diaminomethylene-3-methylsulfonyl-4-(1-propen-1-yl)benzamide, m.p. 223°–225°;

with 3-methylsulfonyl-4-ethenylbenzoyl chloride,
   N-diaminomethylene-3-methylsulfonyl-4-ethenylbenzamide;

with 3-methylsulfonyl-4-(1-propen-2-yl)benzoyl chloride,
   N-diaminomethylene-3-methylsulfonyl-4-(1-propen-2-yl)benzamide;

with 3-methylsulfonyl-4-(1-propen-3-yl)benzoyl chloride,
   N-diaminomethylene-3-methylsulfonyl-4-(1-propen-3-yl)benzamide;

with 3-methylsulfonyl-4-(1-buten-4-yl)benzoyl chloride,
   N-diaminomethylene-3-methylsulfonyl-4-(1-buten-4-yl)benzamide;

with 3-methylsulfonyl-4-(3-methylsulfonyl-1-propen-1-yl)benzoyl chloride,
   N-diaminomethylene-3-methylsulfonyl-4-(3-methylsulfonyl-1-propen-1-yl)benzamide;

with 3-methylsulfonyl-4-(2-buten-1-yl)benzoyl chloride,
   N-diaminomethylene-3-methylsulfonyl-4-(2-buten-1-yl)benzamide;

with 3-methylsulfonyl-4-(2-buten-2-yl)benzoyl chloride,
   N-diaminomethylene-3-methylsulfonyl-4-(2-buten-2-yl)benzamide;

with 3-methylsulfonyl-4-(3-methyl-2-buten-2-yl)benzoyl chloride,
   N-diaminomethylene-3-methylsulfonyl-4-(3-methyl-2-buten-2-yl)benzamide;

with 3-methylsulfonyl-4-(1-buten-3-yl)benzoyl chloride,
   N-diaminomethylene-3-methylsulfonyl-4-(1-buten-3-yl)benzamide;

with 3-methylsulfonyl-4-(1-buten-1-yl)benzoyl chloride,
   N-diaminomethylene-3-methylsulfonyl-4-(1-buten-1-yl)benzamide;

with 3-methylsulfonyl-4-(1-buten-2-yl)benzoyl chloride,
   N-diaminomethylene-3-methyl-4-(1-buten-2-yl)benzamide;

with 3-methylsulfonyl-4-(1-buten-3-yl)benzoyl chloride,
   N-diaminomethylene-3-methylsulfonyl-4-(1-buten-3-yl)benzamide;

with 3-methylsulfonyl-4-(1-penten-1-yl)benzoyl chloride,
   N-diaminomethylene-3-methylsulfonyl-4-(1-penten-1-yl)benzamide;

with 3-methylsulfonyl-4-(2-penten-1-yl)benzoyl chloride,
   N-diaminomethylene-3-methylsulfonyl-4-(2-penten-1-yl)benzamide;

with 3-methylsulfonyl-4-(3-penten-1-yl)benzoyl chloride,
   N-diaminomethylene-3-methylsulfonyl-4-(3-penten-1-yl)benzamide;

with 3-methylsulfonyl-4-(1-hexen-1-yl)benzoyl chloride,
   N-diaminomethylene-3-methylsulfonyl-4-(1-hexen-1-yl)benzamide;

with 3-methylsulfonyl-4-(2-hexen-1-yl)benzoyl chloride,
   N-diaminomethylene-3-methylsulfonyl-4-(2-hexen-1-yl)benzamide;

with 3-methylsulfonyl-4-(3-hexen-1-yl)benzoyl chloride,
   N-diaminomethylene-3-methylsulfonyl-4-(3-hexen-1-yl)benzamide;

Example 6

6.0 g of N-diaminomethylene-2-methyl-4-ethynyl-5-methylsulfonylbenzamide, m.p. 223°–226° [obtainable by reaction of methyl 2-methyl-4-bromo-5-methylsulfonyl-benzoate with Li acetylide to give methyl 2-methyl-4-ethynyl-5-methylsulfonyl-benzoate and subsequent reaction with guanidine] are dissolved in 300 ml of DMF and hydrogenated in the presence of 450 mg of $Pd-CaCO_3$ (Lindlar catalyst) for 15 minutes in a stream of hydrogen (p=1 bar). Customary working up gives N-diaminomethylene-2-methyl-4-ethenyl-5-methylsulfonyl-benzamide).

Analogous hydrogenation with $H_2$ in the presence of the Lindlar catalyst gives with N-diaminomethylene-2-methyl-4-(1-propyn-1-yl)-5-methylsulfonylbenzamide
  N-diaminomethylene-2-methyl-4-(1-propen-1-yl)-5-methylsulfonylbenzamide;
with N-diaminomethylene-2-methyl-4-(1-propyn-3-yl)-5-methylsulfonylbenzamide
  N-diaminomethylene-2-methyl-4-(1-propen-3-yl)-5-methylsulfonylbenzamide;
with N-diaminomethylene-2-ethyl-4-ethynyl-5-methylsulfonylbenzamide
  N-diaminomethylene-2-ethyl-4-ethenyl)-5-methylsulfonylbenzamide;
with N-diaminomethylene-2-ethyl-4-(1-propyn-3-yl)-5-methylsulfonylbenzamide
  N-diaminomethylene-2-ethyl-4-(1-propen-3-yl)-5-methylsulfonylbenzamide;
with N-diaminomethylene-2-ethyl-4-(propyn-1-yl)-5-methylsulfonylbenzamide
  N-diaminomethylene-2-ethyl-4-(1-propen-1-yl)-5-methylsulfonylbenzamide.

Example 7

80 g of bis(benzonitrile)-Pd(II) chloride are added to a solution of 1 g of N-diaminomethylene-2-methyl-4-(1-cyclopenten-3-yl)-5-methylsulfonylbenzamide [obtainable according to Example 1] in 20 ml of toluene and the mixture is boiled under reflux for 2 hours. After filtration, removal of the solvent and customary working up, an isomer mixture consisting of three isomers is then obtained. After pre-purification of the isomer mixture by chromatography (silica gel/ethyl acetate-methanol 9:1), the mixture is introduced, for separation, onto a Prebar$^R$ stainless steel cartridge 250-50, filled with LiChroprep RP-18, and eluted with 0.1 m NaH$_2$PO$_4$ buffer/acetonitrile in a ratio of 9:1 with an ascending gradient up to a ratio of 1:1. This gives:

Isomer 1: N-diaminomethylene-2-methyl-4-(1-cyclopenten-3-yl)-5-methylsulfonylbenzamide, m.p. 184°–186° (14%);
Isomer 2: N-diaminomethylene-2-methyl-4-(1-cyclopenten-1-yl)-5-methylsulfonylbenzamide, m.p. 138°–140° (42%);
Isomer 3: N-diaminomethylene-2-methyl-4-(1-cyclopenten-4-yl)-5-methylsulfonylbenzamide (44%)

Example 8

Analogously to Example 7, isomerization of 3.1 g of N-diaminomethylene-2-ethyl-4-(1-cyclopenten-3-yl)-5-methylsulfonylbenzamide [obtainable according to Example 2] in the presence of bis(benzonitrile)-Pd(II) chloride gives:
Isomer 1: N-diaminomethylene-2-ethyl-4-(1-cyclopenten-3-yl)-5-methylsulfonylbenzamide;
Isomer 2: N-diaminomethylene-2-ethyl-4-(1-cyclopenten-1-yl)-5-methylsulfonylbenzamide;
Isomer 3: N-diaminomethylene-2-ethyl-4-(1-cyclopenten-4-yl)-5-methylsulfonylbenzamide.

Example 9

Analogously to Example 1, reaction of 1.8 g of 2-methyl-4-(1-cyclopenten-3-yl)-5-nitrobenzoyl chloride with guanidine gives, after customary working up, N-diaminomethylene-2-methyl-4-(1-cyclopenten-3-yl)-5-nitrobenzamide, which can be recrystallized from acetonitrile/diethyl ether.

Analogous reaction of guanidine gives
with 2-methyl-4-(1-propen-1-yl)-5-nitrobenzoyl chloride
  N-diaminomethylene-2-methyl-4-(1-propen-1-yl)-5-nitrobenzamide;
with 2-methyl-4-ethenyl-5-nitrobenzoyl chloride
  N-diaminomethylene-2-methyl-4-ethenyl-5-nitrobenzamide;
with 2-methyl-4-(1-propen-2-yl)-5-nitrobenzoyl chloride
  N-diaminomethylene-2-methyl-4-(1-propen-2-yl)-5-nitrobenzamide;
with 2-methyl-4-(1-propen-3-yl)-5-nitrobenzoyl chloride
  N-diaminomethylene-2-methyl-4-(1-propen-3-yl)-5-nitrobenzamide;
with 2-methyl-4-(1-buten-4-yl)-5-nitrobenzoyl chloride
  N-diaminomethylene-2-methyl-4-(1-buten-4-yl)-5-nitrobenzamide;
with 2-methyl-4-(2-methyl-1-propen-1-yl)-5-nitro-benzoyl chloride
  N-diaminomethylene-2-methyl-4-(2-methyl-1-propen-1-yl)-5-nitrobenzamide;
with 2-methyl-4-(2-buten-1-yl)-5-nitrobenzoyl chloride
  N-diaminomethylene-2-methyl-4-(2-buten-1-yl)-5-nitrobenzamide;
with 2-methyl-4-(2-buten-2-yl)-5-nitrobenzoyl chloride
  N-diaminomethylene-2-methyl-4-(2-buten-2-yl)-5-nitrobenzamide;
with 2-methyl-4-(3-methyl-2-buten-2-yl)-5-nitrobenzoyl chloride
  N-diaminomethylene-2-methyl-4-(3-methyl-2-buten-2-yl)-5-nitrobenzamide;
with 2-methyl-4-(1-buten-3-yl)-5-nitrobenzoyl chloride
  N-diaminomethylene-2-methyl-4-(1-buten-3-yl)-5-nitrobenzamide;
with 2-methyl-4-(1-buten-1-yl)-5-nitrobenzoyl chloride
  N-diaminomethylene-2-methyl-4-(1-buten-1-yl)-5-nitrobenzamide;
with 2-methyl-4-(1-buten-2-yl)-5-nitrobenzoyl chloride
  N-diaminomethylene-2-methyl-4-(1-buten-2-yl)-5-nitrobenzamide;
with 2-methyl-4-(1-buten-3-yl)-5-nitrobenzoyl chloride
  N-diaminomethylene-2-methyl-4-(1-buten-3-yl)-5-nitrobenzamide;
with 2-methyl-4-(1-penten-1-yl)-5-nitrobenzoyl chloride
  N-diaminomethylene-2-methyl-4-(1-penten-1-yl)-5-nitrobenzamide;
with 2-methyl-4-(2-penten-1-yl)-5-nitrobenzoyl chloride
  N-diaminomethylene-2-methyl-4-(2-penten-1-yl)-5-nitrobenzamide;
with 2-methyl-4-(3-penten-1-yl)-5-nitrobenzoyl chloride
  N-diaminomethylene-2-methyl-4-(3-penten-1-yl)-5-nitrobenzamide;
with 2-methyl-4-(1-hexen-1-yl)-5-nitrobenzoyl chloride
  N-diaminomethylene-2-methyl-4-(1-hexen-1-yl)-5-nitrobenzamide;
with 2-methyl-4-2-hexen-1-yl)-5-nitrobenzoyl chloride
  N-diaminomethylene-2-methyl-4-(2-hexen-1-yl)-5-nitrobenzamide;
with 2-methyl-4-(3-hexen-1-yl)-5-nitrobenzoyl chloride
  N-diaminomethylene-2-methyl-4-(3-hexen-1-yl)-5-nitrobenzamide;

Example 10

Analogously to Example 1, reaction of 1.8 g of 2-methyl-4-(1-cyclopenten-3-yl)-5-trifluoromethylbenzoyl chloride with guanidine gives, after customary working up, N-diaminomethylene-2-methyl-4-(1-cyclopenten-3-yl)5-trifluoromethylbenzamide, which can be recrystallized from acetonitrile/diethylether.

Analogous reaction of guanidine gives with 2-methyl-4-(1-propen-1-yl)-5-trifluoromethylbenzoyl chloride
N-diaminomethylene-2-methyl-4-(1-propen-1-yl)-5-trifluoromethylbenzamide;

with 2-methyl-4-ethenyl-5-trifluoromethylbenzoyl chloride
N-diaminomethylene-2-methyl-4-ethenyl-5-trifluoromethylbenzamide;

with 2-methyl-4-(1-propen-2-yl)-5-trifluoromethylbenzoyl chloride
N-diaminomethylene-2-methyl-4-(1-propen-2-yl)-5-trifluoromethylbenzamide;

with 2-methyl-4-(1-propen-3-yl)-5-trifluoromethylbenzoyl chloride
N-diaminomethylene-2-methyl-4-(1-propen-3-yl)-5-trifluoromethylbenzamide;

with 2-methyl-4-(1-buten-4-yl)-5-trifluoromethylbenzoyl chloride
N-diaminomethylene-2-methyl-4-(1-buten-4-yl)-5-trifluoromethylbenzamide;

with 2-methyl-4-(2-methyl-1-propen-1-yl)-5-trifluoromethylbenzoyl chloride
N-diaminomethylene-2-methyl-4-(2-methyl-1-propen-1-yl)-5-trifluoromethylbenzamide;

with 2-methyl-4-(2-buten-1-yl)-5-trifluoromethylbenzoyl chloride
N-diaminomethylene-2-methyl-4-(2-buten-1-yl)-5-trifluoromethylbenzamide;

with 2-methyl-4-(2-buten-2-yl)-5-trifluoromethylbenzoyl chloride
N-diaminomethylene-2-methyl-4-(2-buten-2-yl)-5-trifluoromethylbenzamide;

with 2-methyl-4-(3-methyl-2-buten-2-yl)-5-trifluoromethylbenzoyl chloride
N-diaminomethylene-2-methyl-4-(3-methyl-2-buten-2-yl)-5-trifluoromethylbenzamide;

with 2-methyl-4-(1-buten-3-yl)-5-trifluoromethylbenzoyl chloride
N-diaminomethylene-2-methyl-4-(1-buten-3-yl)-5-trifluoromethylbenzamide;

with 2-methyl-4-(1-buten-1-yl)-5-trifluoromethylbenzoyl chloride
N-diaminomethylene-2-methyl-4-(1-buten-1-yl)-5-trifluoromethylbenzamide;

with 2-methyl-4-(1-buten-2-yl)-5-trifluoromethylbenzoyl chloride
N-diaminomethylene-2-methyl-4-(1-buten-2-yl)-5-trifluoromethylbenzamide;

with 2-methyl-4-(1-buten-3-yl)-5-trifluoromethylbenzoyl chloride
N-diaminomethylene-2-methyl-4-(1-buten-3-yl)-5-trifluoromethylbenzamide;

with 2-methyl-4-(1-penten-1-yl)-5-trifluoromethyl-benzoyl chloride
N-diaminomethylene-2-methyl-4-(1-penten-1-yl)-5-trifluoromethylbenzamide;

with 2-methyl-4-(2-penten-1-yl)-5-trifluoromethyl-benzoyl chloride
N-diaminomethylene-2-methyl-4-(2-penten-1-yl)-5-trifluoromethylbenzamide;

with 2-methyl-4-(3-penten-1-yl)-5-trifluoromethyl-benzoyl chloride
N-diaminomethylene-2-methyl-4-(3-penten-1-yl)-5-trifluoromethylbenzamide;

with 2-methyl-4-(1-hexen-1-yl)-5-trifluoromethylbenzoyl chloride
N-diaminomethylene-2-methyl-4-(1-hexen-1-yl)-5-trifluoromethylbenzamide;

with 2-methyl-4-(2-hexen-1-yl)-5-trifluoromethylbenzoyl chloride
N-diaminomethylene-2-methyl-4-(2-hexen-1-yl)-5-trifluoromethylbenzamide;

with 2-methyl-4-(3-hexen-1-yl)-5-trifluoromethylbenzoyl chloride
N-diaminomethylene-2-methyl-4-(3-hexen-1-yl)-5-trifluoromethylbenzamide;

Example 11

Analogously to Example 1, reaction of 1.8 g of 2-methyl-4-(1-cyclohexen-3-yl)-5-methylsulfonylbenzoyl chloride with guanidine gives, after customary working up, N-diaminomethylene-2-methyl-4-(1-cyclohexen-3-yl)-5-methylsulfonylbenzamide, which can be recrystallized from acetonitrile/diethyl ether.

Analogous reaction of guanidine gives with 2-methyl-4-(1-cyclohexen-3-yl)-5-nitrobenzoyl chloride
N-diaminomethylene-2-methyl-4-(1-cyclohexen-3-yl)-5-nitrobenzamide;

with 2-methyl-4-(1-cyclohexen-3-yl)-5-trifluorobenzoyl chloride
N-diaminomethylene-2-methyl-4-(1-cyclohexen-3-yl)-5-trifluorobenzamide;

with 2-methyl-4-(1-cyclohexen-3-yl)-5-nitrobenzoyl chloride
N-diaminomethylene-2-ethyl-4-(1-cyclohexen-3-yl)-5-nitrobenzamide;

Example 12

Analogously to Example 7, isomerization of 2.3 g of N-diaminomethylene-2-methyl-4-(1-cyclohexen-3-yl)-5-methylsulfonylbenzamide [obtainable according to Example 11] in the presence of bis(benzonitrile)-Pd(II) chloride gives:

Isomer 1: N-diaminomethylene-2-methyl-4-(1-cyclohexen-3-yl)-5-methylsulfonylbenzamide;

Isomer 2: N-diaminomethylene-2-methyl-4-(1-cyclohexen-1-yl)-5-methylsulfonylbenzamide;

Isomer 3: N-diaminomethylene-2-methyl-4-(1-cyclohexen-4-yl)-5-methylsulfonylbenzamide.

The following examples relate to pharmaceutical formulations:

Example A: Injection Vials

A solution of 100 g of an active compound of the formula I and 5 g of disodium hydrogen phosphate in 3 1 of double-distilled water is adjusted to pH 6.5 with 2 N hydrochloric acid, subjected to sterile filtration, bottled in injection vials, lyophilized under sterile conditions and closed in a sterile manner. Each injection vial contains 5 mg of active compound.

Example B: Suppositories

A mixture of 20 g of an active compound of the formula I is melted with 100 g of soya lecithin and 1400 g of cocoa butter, and the mixture is poured into molds and allowed to cool. Each suppository comprises 20 mg of active compound.

Example C: Solution

A solution of 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water is prepared. The pH is adjusted to 6.8 and the solution is made up to 1 l and sterilized by irradiation. This solution can be used in the form of eyedrops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is pressed to tablets in the customary manner such that each tablet comprises 10 mg of active compound.

Example F: Coated Tablets

Tablets are pressed analogously to Example E and are then coated with a coating of sucrose, potato starch, talc, tragacanth and colorant in the customary manner.

Example G: Capsules 2 kg of active compound of the formula I are introduced into hard gelatin capsules in the customary manner such that each capsule contains 20 mg of the active compound.

Example H: Ampules

A solution of 1 kg of active compound of the formula I in 60 l of double-distilled water is subjected to sterile filtration, bottled in ampules, lyophilized under sterile conditions and closed in a sterile manner. Each ampule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can made various changes and modifications of the invention to adapt it to various usages and conditions.

We claim:

1. An alkenyl-benzoylguanidine compound of the formula I

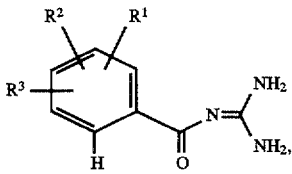

wherein $R^1$ is in the position on the ring ortho to the guanidine group and is Hal, A, CN, $NO_2$, $CF_3$, $CH_2F$, $CHF_2$, $C_2F_5$ or $CH_2CF_3$, $R^2$ is H, Hal, A, CN, $NO_2$, $CF_3$, $CH_2F$, $CHF_2$, $C_2F_5$, $CH_2CF_3$ or $SO_n-R_4$, $R^3$ is $-CR^5=CR^6R^7$, $-C(R^6R^5)-CR^7=CR^9R^8$, $-C(R^6R^5)-C(R^7R^8)-CR^9=CR^{10}R^{11}$ or cycloalkenyl having 3-7 C atoms or cycloalkenylalkyl having 4-8 C atoms, $R^4$ is A or Ph, $R^5$, $R^6$, $R^7$, $R^8$, $R^9$, $R^{10}$, and $R^{11}$ in each case independently of one another are H or A, A is alkyl having 1 to 6 C atoms Hal is F, Cl, Br or I, Ph is phenyl which is unsubstituted or mono-, di- or trisubstituted by A, OA, $NH_2$, $NR^4R^5$, F, Cl, Br, I or $CF_3$, n is 1 or 2, or a physiologically acceptable salt thereof.

2. A compound of the formula I of claim 1, which is (a) N-diaminomethylene-2-methyl-4-(1-cyclopenten-3-yl)-5-methylsulfonylbenzamide;

(b) N-diaminomethylene-2-methyl-4-(1-propen-1-yl)-5-methylsulfonylbenzamide;

(c) N-diaminomethylene-2-ethenyl-5-methylsulfonylbenzamide;

(d) N-diaminomethylene-2-methyl-4-(1-cyclopenten-1-yl)-5-methylsulfonylbenzamide;

(e) N-diaminomethylene-2-methyl-4-(1-propen-3-yl)-5-methylsulfonylbenzamide;

(f) N-diaminomethylene-2-methyl-4-(1-cyclohexen-3-yl)-5-methylsulfonylbenzamide; or a physiologically acceptable salt thereof.

3. A process for the preparation of an alkylbenzoylguanidine compound of the formula I according to claim 1 or a salt thereof, comprising reacting a compound of the formula II

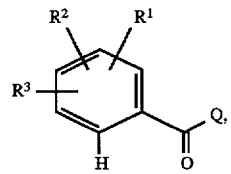

wherein $R^1$, $R^2$ and $R^3$ have the above-mentioned meanings and

Q is Cl, Br, OA, O—CO—A, O—CO—Ph, OH or another reactive esterified OH group or leaving group which can easily be replaced nucleophilically, with guanidine, or reacting a benzoylguanidine of the formula III

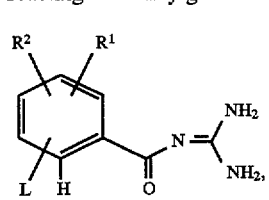

wherein $R^1$ and $R^2$ have the above-mentioned meanings and

L is F, Cl, Br or I, with an unsaturated hydrocarbon compound of the formula IV $$R^3-H \qquad IV$$

wherein $R^3$ has the meaning given, in the presence of a transition metal catalyst and if appropriate of an activator, or treating with a reducing agent a compound which otherwise corresponds to the formula I but which contains, instead of one or more hydrogen atoms, one or more reducible group(s), or treating with a solvolyzing agent a compound which otherwise corresponds to the formula I but which contains, instead of one or more hydrogen atoms, one or more solvolyzable group(s), or converting a radical $R^3$ into another radical $R^3$ by isomerization, by rearranging a double bond under the action of a transition metal catalyst and/or of a metal carbonyl, and/or converting a base of the formula I into one of its salts by treatment with an acid.

4. A process for the preparation of a pharmaceutical formulation comprising bringing a compound of the formula I according to claim 1 and/or one of its physiologically acceptable salts into a suitable dosage form together with at least one solid, liquid or semi-liquid carrier or auxiliary.

5. A pharmaceutical composition comprising at least one compound of the formula I according to claim 1 and/or one of its physiologically acceptable salts and at least one solid, liquid or semi-liquid carrier or auxiliary.

6. A method for the treatment or preventive treatment of arrhythmias, angina pectoris and infarcts which comprises administering to a subject in need thereof a disease controlling effective amount of a compound of the formula I of claim 1 or a physiologically acceptable salt thereof.

7. A method for treating or controlling a disease treatable by inhibition of the cellular $Na^+/H^+$antiporter which comprises administering a cellular $Na^+/H^+$antiporter inhibiting effective amount of an alkenyl-benzoylguanidine of claim 1 to a human or animal in need thereof.

8. The method of claim 7, wherein the alkenyl-benzoylguanidine is administered in a daily dose of 0.0001–0.1 mg/kg of body weight.

9. The method of claim 6, wherein the compound of the formula I is administered in a daily dose of 0.0001–0.1 mg/kg of body weight.

10. A method which comprises administering an effective amount of an alkenyl-benzoylguanidine of claim 1 to a human or animal in need thereof in a surgical operation for protection of an under-supplied organ, in an organ transplant for protection of removed organs, in an angioplastic operation on a vessel or the heart, in an ischaemia of the nervous system, in the treatment of a state of shock or for the preventive avoidance of essential hypertension.

11. The alkenyl-benzoylguanidine compound of claim 1, wherein $R^1$ is A and $R^2$ is $—SO_2—A$, $NO_2$ or $CF_3$.

12. The alkenyl-benzoylguanidine compound of claim 1, wherein $R^1$ is Hal and $R_2$ is $—SO_2A$, $NO_2$ or $CF_3$.

13. The alkenyl-benzoylguanidine compound of claim 1, wherein $R^1$ is A, $R^2$ is $—SO_2A$ and $R^3$ is $—CR^5=CR^6R^7$, where $R^5$ to $R^7$ in each case independently of one another are H or methyl.

14. The alkenyl-benzoylguanidine compound of claim 1, wherein $R^1$ is A, $R^2$ is $—SO_2—A$ and $R^3$ is $—C(R^5 R^6)—CR^7=CR^8R^9$ where $R^5$ to $R^9$ in each case independently of one another are H or methyl.

15. The alkenyl-benzoylguanidine compound of claim 1, wherein $R^1$ is A, $R^2$ is $—SO_2—A$ and $R^3$ is $—C(R^5R^6)—C(R^7R^8)—CR^9=CR^{10}R^{11}$, where $R^5$ to $R^{11}$ in each case independently of one another are H or methyl.

16. The alkenyl-benzoylguanidine compound of claim 1, wherein $R^2$ is $—SO_2—A$ and is in the meta-position relative to the benzoylguanidine group.

17. The alkenyl-benzoylguanidine compound of claim 1, wherein $R^3$ is cycloalkenyl having 3–7 C atoms and is in the para-position relative to the benzoylguanidine group and $R^2$ is in the meta-position relative to the benzoylguanidine group and is $—SO_2—A$.

18. The alkenyl-benzoylguanidine compound of claim 1, wherein $R^1$ is A, $R^2$ is $—SO^2—A$, $R^3$ is cycloalkenyl having 3 to 7 C atoms and $R^3$ is located in the para-position relative to the benzoylguanidine group.

\* \* \* \* \*